US00PP37545P2

(12) United States Plant Patent
Carter

(10) Patent No.: US PP37,545 P2
(45) Date of Patent: Jul. 28, 2026

(54) ***SALVIA* PLANT NAMED 'Hummingbird Falls Sky Blue'**

(50) Latin Name: ***Salvia* x *guaranitica***
Varietal Denomination: Hummingbird Falls Sky Blue

(71) Applicant: Kermit E. Carter, Elk, CA (US)

(72) Inventor: Kermit E. Carter, Elk, CA (US)

( * ) Notice: Subject to any disclaimer, the term of this patent is extended or adjusted under 35 U.S.C. 154(b) by 0 days.

(21) Appl. No.: 19/397,203

(22) Filed: Nov. 21, 2025

(51) Int. Cl.
*A01H 5/02* (2018.01)
*A01H 6/50* (2018.01)

(52) U.S. Cl.
USPC ..... Plt./475

(58) Field of Classification Search
USPC ..... Plt./475
See application file for complete search history.

(56) References Cited

U.S. PATENT DOCUMENTS

PP29,585 P2 * 8/2018 Carter ..... Plt./475

* cited by examiner

*Primary Examiner* — Susan McCormick Ewoldt
(74) *Attorney, Agent, or Firm* — Weatherly IP Solutions, LLC; James M. Weatherly

(57) ABSTRACT

A new cultivar of *Salvia* named 'Hummingbird Falls Sky Blue' that is distinguishable by pendulous compact growth habit, arching plant habit and small deep green leaves, The flowers of 'Hummingbird Falls Sky Blue' are bright sky blue in color and the inflorescence calyces are black in conditions of full sunlight and which persist after flowering is finished.

2 Drawing Sheets

Genus and species: *Salvia* x *guaranitica.*
Variety denomination: 'Hummingbird Falls Sky Blue'.

BACKGROUND

The present disclosure relates to a new and distinct cultivar of *Salvia* plant, species *guaranitica,* also known as anise-scented sage or hummingbird sage, a perennial that is grown for use as an ornamental landscape and container plant. The new variety is known botanically as *Salvia* x *guaranitica* and will be referred to hereinafter by the cultivar name 'Hummingbird Falls Sky Blue'.

'Hummingbird Falls Sky Blue' was selected in April 2022 from a population of seedlings which the inventor had raised from seed resulting from the controlled pollination of a proprietary selection (unpatented and unreleased) of *Salvia guaranitica* known to the inventor as *Salvia* '2021-005' as male parent and the inventor's variety *Salvia* x *guaranitica* 'Hummingbird Falls' (U.S. Plant Pat. No. 33,891) as female parent. The hybridization was carried out in July 2021 when the inventor applied pollen from the male parent to the female parent plant at the inventor's nursery in Elk, California.

'Hummingbird Falls Sky Blue' was selected by the inventor for its exceptionally compact and pendulous growth habit, small leaves and profuse branching and lighter and brighter blue flowers in comparison with the inventor's variety 'Hummingbird Falls'. Both varieties 'Hummingbird Falls' and 'Hummingbird Falls Sky Blue' are well-suited to production and sale in hanging baskets.

'Hummingbird Falls Sky Blue' was first asexually propagated in the fall of 2023 in a greenhouse at the inventor's nursery in Elk, California using softwood tip cuttings. The inventor has determined during successive cycles of asexual propagation that 'Hummingbird Falls Sky Blue' is stable and reproduces true to type.

SUMMARY

The following traits have been repeatedly observed and represent the distinguishing characteristics of 'Hummingbird Falls Sky Blue'. 'Hummingbird Falls Sky Blue' has not been tested under all possible conditions and phenotypic differences may be observed with variations in environmental, climatic, and cultural conditions, without however, any variance in genotype.

1. 'Hummingbird Falls Sky Blue' exhibits a compact plant habit with profuse branching.
2. The stems of 'Hummingbird Falls Sky Blue' are thin in comparison with the species, such that the stems arch as they grow longer and under the weight of their terminal inflorescences.
3. The flowers of 'Hummingbird Falls Sky Blue' are vibrant bright sky blue in color.
4. 'Hummingbird Falls Sky Blue' grows and flowers rapidly. Flowering plants may be produced in 10 to 12 weeks from a cutting. A flowering hanging basket may be produced in three months from planting a 3 months old starter plant.
5. The calyces of the flowers of 'Hummingbird Falls Sky Blue' range in color from very dark purple to black. The calyces are black in conditions of full sunlight.
6. The calyces (sepals) of 'Hummingbird Falls Sky Blue' persist after flowering has finished. The once-flowering inflorescences continue to display attractive and contrasting black calyces.
7. 'Hummingbird Falls Sky Blue' produces new flowering stems continuously from spring to fall.

8. The leaves of 'Hummingbird Falls Sky Blue' are small and dark green in color at all stages of growth.

DESCRIPTION OF THE PHOTOGRAPHS

The accompanying color photographs illustrate the overall appearance of the new *Salvia* cultivar 'Hummingbird Falls Sky Blue' showing the colors as true as it is reasonably possible to obtain in colored reproductions of this type. The photographs were taken in early November 2025 from a plant which was six months old and which had been grown for three months as a hanging basket out of doors in Santa Barbara, California. The plants had received one low pinch (at 5 cm. above ground level) after initial establishment. Colors in the photographs may differ from the color values cited in the detailed botanical description, which more accurately describes the actual colors of the new variety 'Hummingbird Falls Sky Blue'.

DESCRIPTION OF THE NEW VARIETY

Figure 1:
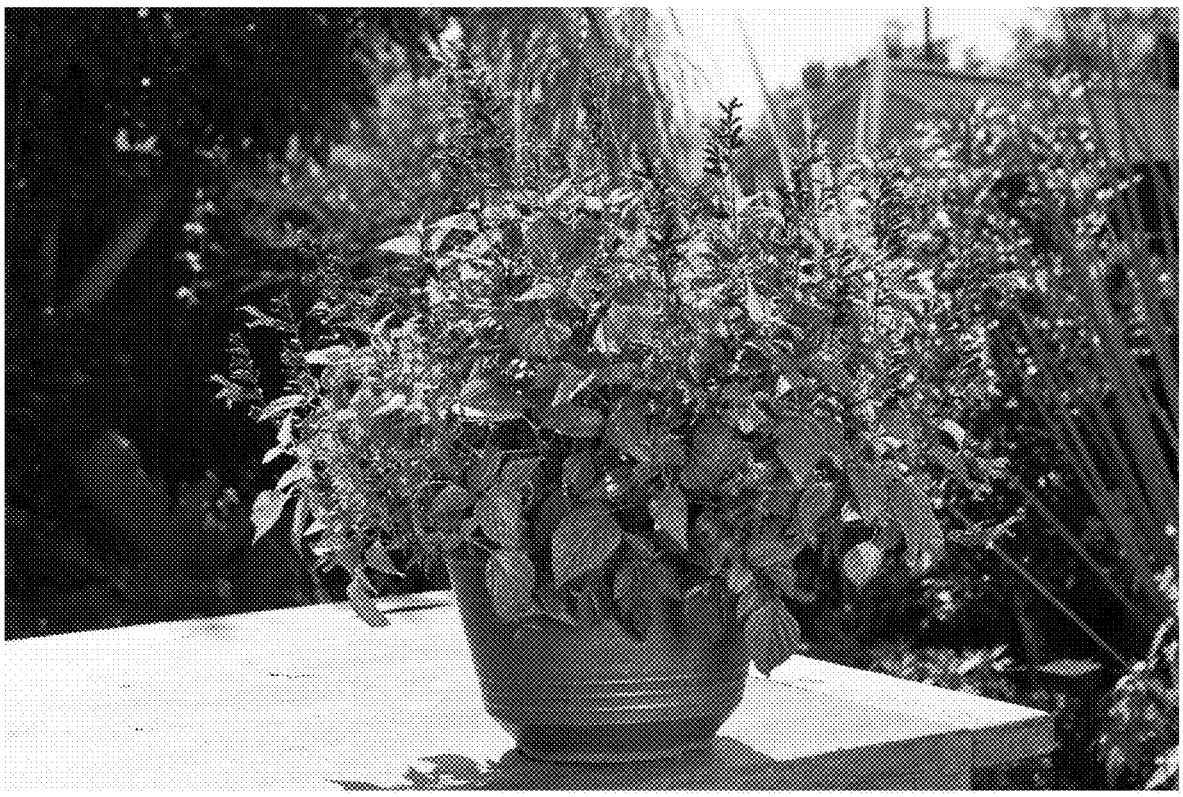
FIG. 1 depicts an entire plant of 'Hummingbird Falls Sky Blue'.
Figure 2:
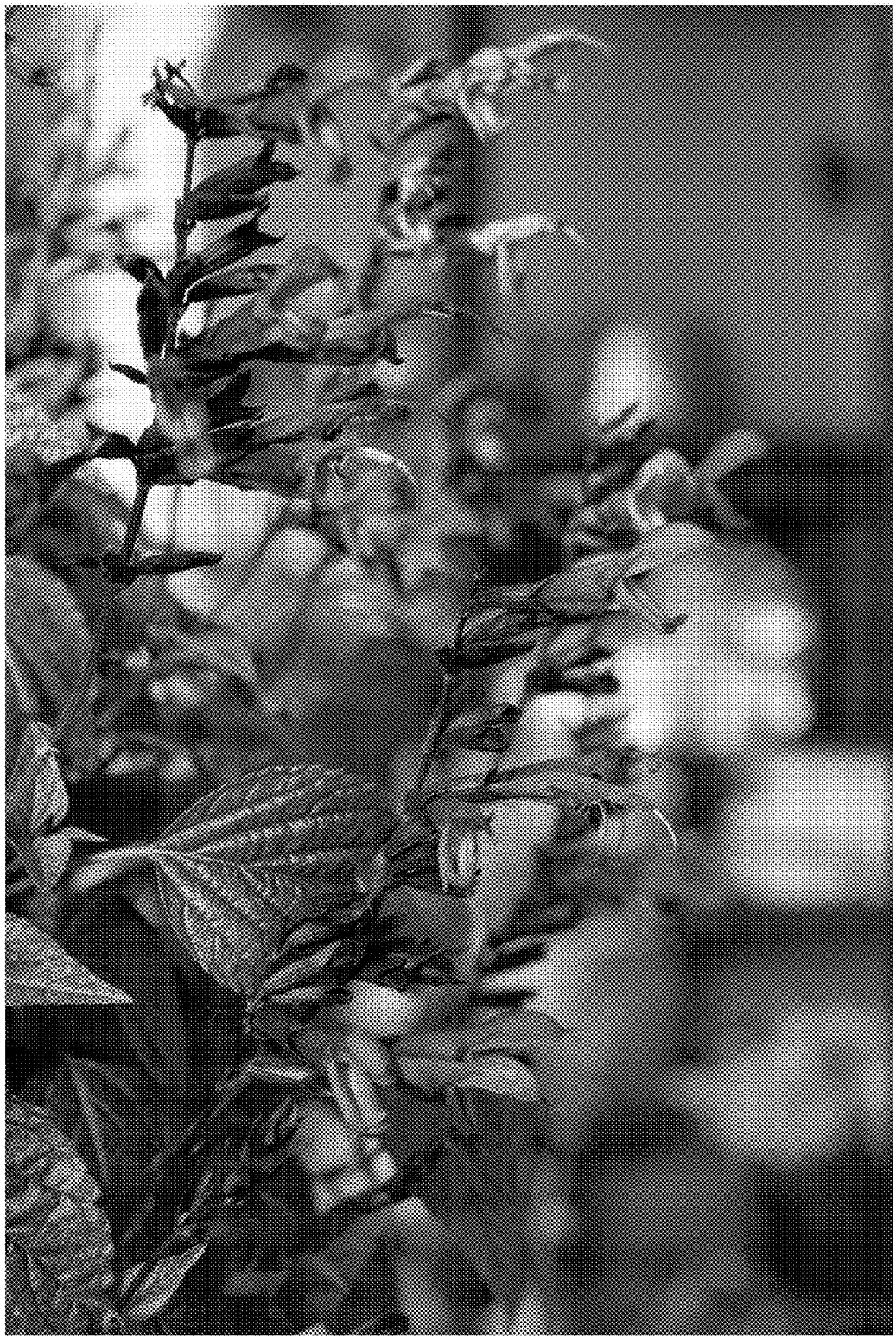
FIG. 2 depicts a close-up view of the inflorescence of 'Hummingbird Falls Sky Blue'.

The following detailed descriptions set forth the distinctive characteristics of 'Hummingbird Falls Sky Blue'. Observations, measurements, values, and comparisons were collected in November 2025 in Santa Barbara, California from a six months old plant grown outdoors in full sun in a 2.5 gallon hanging basket container. Color determinations have been made in accordance with The 2007 Royal Horticultural Society Colour Chart from London England, except where general color terms of ordinary dictionary significance are used.

Classification:

*Family*.—Lamiaceae.

*Genus*.—*Salvia*.

*Species*.—x *guaranitica*.

*Common name*.—Sage.

Parentage:

*Female parent*.—*Salvia* x *guaranitica* 'Hummingbird Falls' (U.S. Plant Pat. No. 33,891).

*Male parent*.—*Salvia* x *guaranitica* '2021 005' (inventor's proprietary unreleased seedling).

Plant:

*Propagation method*.—Softwood tip cuttings.

*Rooting system*.—Fine and fibrous.

*Vigor*.—Moderate vigor.

*Time to develop roots*.—5 days are needed for a cutting to develop roots at recommended rooting temperature of 20° to 22° Centigrade.

*Crop time*.—Approximately 3 months are required to produce a budded and flowering plant in a quart container from a rooted cutting, and a further three months to produce a fully-flowering hanging basket from planting a quart container into a hanging basket container.

*Suggested container size*.—1 gallon container or larger for hanging basket production.

*Use*.—Ornamental for use as a container plant and as a plant for hanging baskets.

*Type*.—Perennial.

*Overall dimensions* (*including inflorescences*).—After one year's growth in a 2.5 gallon container: 36 cm-40 cm in height, and 55 cm-65 cm in width.

*Cultural requirements*.—Grow in full sun with moderate water in free-draining growing medium.

*Hardiness*.—USDA Zone 8.

*Form*.—Bush.

*Growth habit*.—Compact structure with stems which become pendulous with age and when flowering.

*Blooming season*.—From one month after breaking spring dormancy to first frost.

*Lastingness of blooms*.—Inflorescence has some flower for 14 days, individual flowers last for 2 to 3 days.

Stem (basal stem below initial pruning at 5 cm above ground or growing medium level):

*Length*.—5 cm.

*Diameter*.—6 mm.

*Color*.—Brown (165A) striations of thin papery overlaying olive-green (137B) tissue.

*Shape*.—Square, edges rounded.

*Surface texture*.—Chartaceous.

Branches:

*Quantity*.—2 primary branches arising as opposite pairs from uppermost node of stem below point of pruning. 3 secondary branches arising as opposite pairs from nodes along each primary branch.

*Quantity of primary branches*.—10 (1 pair arising from each stem).

*Quantity of secondary branches*.—30 (3 pairs arising from 10 primary branches).

*Primary stem length* (*to base of raceme*).—25 cm to 28 cm.

*Width*.—2.5 mm.

*Internode length*.—Varies between 3.5 cm and 7 cm.

*Color*.—Light olive green 144D towards base, becoming darker 144A towards terminal inflorescence.

*Shape*.—Square, edges rounded.

*Texture*.—Sparsely pubescent. Hairs approximately 1 mm apart, fine and silver-white in color.

Leaves:

*Type, arrangement*.—Simple, opposite.

*Attachment*.—Petiolate.

*Quantity per primary branch*.—3 opposite pairs.

*Quantity per secondary branch*.—3 opposite pairs.

*Shape*.—Deltoid.

*Length*.—Largest leaves (primary branches): 6 cm. leaves typically 5.5 cm-6.0 cm.

*Width*.—Largest leaves (secondary branches) 4 cm., leaves typically 3.5 cm-4.0 cm.

*Margin*.—Dentate, teeth 2.5 mm-3 mm. apart, average 3.5 teeth per 1 cm. of margin.

*Thickness*.—Moderately coarse and stiff.

*Leaf surface texture*.—Wrinkled, matte.

*Venation*.—Pinnate. Veins (adaxial surface): Depressed, color as leaf, 137A. Veins (abaxial surface): Prominently raised, midrib raised 1.5 mm. Vein color (abaxial) 138A.

*Texture* (*adaxial surfaces*).—Smooth, glossy.

*Texture* (*abaxial surface*).—Matte, lightly puberulent.

*Color*.—Adaxial surface: 137A. Abaxial surface: Midway between 137A and 138A.

*Apex*.—Acute.

*Base*.—Acute.

*Fragrance*.—Pleasant sage fragrance when rubbed.

*Stipules*.—Present in pairs at each leaf axil on primary and secondary lateral branches.

*Attachment*.—Sessile.

*Shape*.—Short broadly lanceolate, 1.5 mm. in length, 1 mm. in width.
*Texture*.—Firm, fleshy, sparsely puberulent.
*Color*.—138B.

Petiole:
*Shape* (*all branches*).—Terete, flattened adaxial facing, rounded abaxially.
*Length*.—4.5 cm (oldest leaves, primary branches), 3 cm (oldest leaves, secondary branches).
*Width* (*all petioles*).—1.5 mm.
*Texture*.—Sparsely puberulent.
*Color*.—138A.

Peduncle:
*Length* (*to lowest flower whorl*).—2.5 cm.
*Shape*.—Square.
*Width*.—1.5 mm.-2 mm.
*Texture*.—Smooth, faintly puberulent.
*Color*.—Dark purple, between N92A and N186A147A.

Inflorescence:
*Type*.—Terminal raceme.
*Shape*.—Flattened cross-section, taller vertically, narrower horizontally-laterally.
*Length*.—7 cm-7.5 cm. from base of lowest flower to apex of uppermost flower.
*Width* (*racemes with no open flowers*).—2 cm vertically, 1.5 cm. horizontally.
*Width* (*racemes with open flowers*).—4 cm. vertically, 2.5 cm horizontally.
*Flower arrangement*.—Flowers are arranged in whorls.
*Quantity of flowers*.—A range of 4 to 6 flowers per whorl and up to 7 whorls per raceme.
*Distance between whorls*.—15 mm. between lowermost whorls, elsewhere (upper whorls) 8 mm.-9 mm.
*Flowering season*.—Year round in Southern California and spring to summer elsewhere.
*Lastingness of the flowers* (*on the plant*).—From 8 days in spring to 3 days in summer.

Pedicel:
*Length*.—Short, 3.5 mm.
*Width*.—0.75 mm-1.0 mm.
*Texture*.—Smooth, semi-glossy.
*Color*.—Dark purple, between N92A and N186A.

Calyx:
*Shape*.—Campanulate, flattened laterally, flared towards apex (free sepal zone).
*Dimensions* (*before flowering*).—15 mm. in length, 3 mm. in width.
*Dimensions* (*bearing flowers*).—15 mm. in length, 5 mm. in width.

Sepals:
*Quantity*.—2.
*Fused*.—Longitudinally fused for 75%-80% of overall length.
*Length*.—14 mm. of which 4 mm free and flared.
*Width*.—5 mm when flattened.
*Shape*.—Boat shaped, oblanceolate when flattened.
*Apex*.—Acute.
*Base*.—Acute.
*Margin*.—Entire.
*Texture*.—Adaxial surface: Smooth, glossy, longitudinally ribbed. Ribs 1 mm apart, raised less than 0.1 mm. Abaxial surface: Smooth, glabrous, faint parallel longitudinal ridges.
*Color* (*all surfaces*).—N92A and black, 203A, in conditions of full sunlight.

Flowers:
*Quantity*.—4 flowers per whorl and 5-7 whorls per flowering stem.
*Shape*.—Zygomorphic, tubular, two-lipped.
*Length overall*.—35 mm. from base of corolla tube to apex of hooded lip.
*Height* (*vertically*).—9 mm.
*Width* (*laterally*).—3 mm.
*Lastingness of flowers*.—The inflorescences bear some flower in a 14-day period. Individual flowers last for 2 to 3 days.
*Fragrance*.—Faint sage fragrance.

Bud (as emerges from calyx):
*Shape*.—Ovoid, club-shaped.
*Length*.—5 mm to 6 mm.
*Width*.—3 mm to 4 mm.
*Texture*.—Pubescent, especially apex which already bears dense cluster of hairs on future upper petal lip.
*Color* (*hairs*).—N92C.

Corolla:
*Shape*.—Tubular, wider towards base.
*Length*.—7 mm.
*Width*.—2 mm. 3 mm. at and close to base.
*Texture*.—Glabrous.
*Color* (*inner and outer surfaces*).—Bright white, translucent, NN155D.

Petals:
*Quantity*.—2.
*Arrangement*.—One upper petal appearing as a hood, and one lower petal which appears as a large prominent lip.
*Fused*.—Upper and lower petals fused towards corolla tube.
*Upper petal*.—Aspect: Horizontal to slightly elevated. Shape: Hood. Length: 3.0 cm (including corolla tube). Width (flattened): 7 mm. Texture: Adaxial surface: Above corolla tube slightly rough, hood apex puberulent, hairs very short, 0.5 mm. or less in length, color 86A. Abaxial surface: Glabrous, with faint parallel ribs approximately 0.25 mm. apart. Upper petal apex: Rounded. Upper petal base: Truncate with lower lip at corolla mouth. Margin: Smooth, entire. Upper petal color: N89C.
*Lower petal, lip*.—Aspect: Downward, between 45° and 50° below horizontal. Shape: Two-parted, fused longitudinally, sulcate. Length: 10 mm (free of upper petal). Width: 6 mm. Texture (both surfaces): Smooth, glabrous. Apex: Emarginate, depth of notch 0.5 mm.-1 mm. Base: Truncate. Margin: Gently undulating. Color (both surfaces): 86A-86C.

Reproductive organs:
*Stamens*.—Quantity: 2, basally fused and adnate to corolla tube wall. Filaments: Length: 18 mm. of which 4 mm exserted from flower (upper lip) apex. Color: 85B. Anther: Shape: Narrowly elliptical, centrally dorsifixed. Length: 3 mm. Width: 0.5 mm. Color: 196A. Pollen: None present.
*Pistil*.—Quantity: 1. Stigma: Shape: Cleft, forked, 2 arms, each 4 mm in length, less than 0.5 mm. in diameter. Color: 92D. Style: Shape: Tubular. Length: 35 mm. Color: 85D.
*Ovary*.—Absent.
*Seed* (*observed by inventor at inventor's nursery*).—Shape: Ovoid, tiny, less than 1 mm. in diameter and length. Color: Black, 203A Quantity: Very sparse.

Disease and pest susceptibility: Susceptible to sucking insects when stressed. Generally outgrows most bacterial and viral infections. Resistant to deer and rabbit grazing.

Drought tolerance: Drought tolerant.

Heat Tolerance: Very well adapted to high heat when well-watered. High humidity does not impede growth.

COMPARISON WITH PARENTAL LINES AND KNOWN VARIETY

'Hummingbird Falls Sky Blue' is distinguishable from each of its parents and from all other varieties of *Salvia* x *guaranitica* known to the inventor by its pendulous habit and small leaves. by the color and texture of its foliage which is deeper green and thicker than either parent and by the larger size and quantity and the deeper and more intense color of its flowers.

The variety of *Salvia* x *guaranitica* which the inventor considers to be most similar to 'Hummingbird Falls Sky Blue' is the inventor's variety of *Salvia* plant named 'Rhythm & Blues' (U.S. Plant Pat. No. 29,585). Whereas 'Rhythm and Blues' exhibits similar violet-blue flower colors and dark green foliage, the growth habit is strongly upright, with leaves which are approximately 50% larger and whose calyces fall away after flowering. In comparison with 'Rhythm & Blues', 'Hummingbird Falls Sky Blue' exhibits a pendulous plant habit, with smaller foliage and which continues to hold its black calyces after flowering is finished.

I claim:

1. A new and distinct cultivar of *Salvia* plant named 'Hummingbird Falls Sky Blue' as described and illustrated herein.

* * * * *